(12) United States Patent
Polejaev et al.

(10) Patent No.: US 12,402,775 B2
(45) Date of Patent: *Sep. 2, 2025

(54) DEPTH AND CONTOUR DETECTION FOR ANATOMICAL TARGETS

(71) Applicant: GYRUS ACMI, INC., Westborough, MA (US)

(72) Inventors: Vladimir Polejaev, Middletown, CT (US); Kurt G. Shelton, Bedford, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/762,891

(22) Filed: Jul. 3, 2024

(65) Prior Publication Data
US 2024/0349987 A1 Oct. 24, 2024

Related U.S. Application Data

(63) Continuation of application No. 17/393,710, filed on Aug. 4, 2021, now Pat. No. 12,053,149.
(Continued)

(51) Int. Cl.
*A61B 1/00* (2006.01)
*A61B 1/05* (2006.01)
(Continued)

(52) U.S. Cl.
CPC ............ *A61B 1/0005* (2013.01); *A61B 1/063* (2013.01); *A61B 1/0669* (2013.01); *A61B 1/07* (2013.01);
(Continued)

(58) Field of Classification Search
CPC ..... A61B 1/0005; A61B 1/063; A61B 1/0669; A61B 1/07; A61B 1/313; A61B 1/05;
(Continued)

(56) References Cited

U.S. PATENT DOCUMENTS

| 5,557,324 A | 9/1996 | Wolff |
| 6,554,824 B2 | 4/2003 | Davenport et al. |

(Continued)

FOREIGN PATENT DOCUMENTS

| CN | 116056621 A | 5/2023 |
| DE | 112021004183 T5 | 6/2023 |

(Continued)

OTHER PUBLICATIONS

U.S. Appl. No. 17/393,710 U.S. Pat. No. 12,053,149, filed Aug. 4, 2021, Depth and Contour Detection for Anatomical Targets.
(Continued)

*Primary Examiner* — Nasim N Nirjhar
(74) *Attorney, Agent, or Firm* — Schwegman Lundberg & Woessner, P.A.

(57) ABSTRACT

Techniques for detecting depth contours of an anatomical target and for enhancing imaging of the anatomical target are provided. In an example, a reference pattern of light can be projected across an anatomical target and an image of the reflected light pattern upon the anatomical target can be captured. The captured light pattern can be analyzed to determine contour information, which can then be used to provide 3D cues to enhance a 2-dimensional image of the anatomical target.

20 Claims, 6 Drawing Sheets

Related U.S. Application Data

(60) Provisional application No. 63/061,249, filed on Aug. 5, 2020.

(51) Int. Cl.
  *A61B 1/06* (2006.01)
  *A61B 1/07* (2006.01)
  *A61B 1/313* (2006.01)
  *G06T 7/521* (2017.01)
  *G06T 15/80* (2011.01)
  *H04N 23/50* (2023.01)
  *H04N 23/56* (2023.01)

(52) U.S. Cl.
  CPC .............. *A61B 1/313* (2013.01); *G06T 7/521* (2017.01); *G06T 15/80* (2013.01); *H04N 23/56* (2023.01); *A61B 1/05* (2013.01); *G06T 2207/10068* (2013.01); *H04N 23/555* (2023.01)

(58) Field of Classification Search
  CPC . A61B 1/0605; A61B 1/0646; A61B 1/00009; G06T 7/521; G06T 15/80; G06T 2207/10068; G06T 2207/30084; G06T 7/0012; G06T 2207/30096; H04N 5/2256; H04N 2005/2255
  See application file for complete search history.

(56) References Cited

U.S. PATENT DOCUMENTS

| | | |
|---|---|---|
| 8,451,452 B2 | 5/2013 | Podoleanu et al. |
| 9,017,316 B2 | 4/2015 | Khatchaturov et al. |
| 9,445,871 B2 | 9/2016 | Kang et al. |
| 9,486,286 B2 | 11/2016 | Hodel et al. |
| 9,757,199 B2 | 9/2017 | Chia et al. |
| 9,949,615 B2 | 4/2018 | Zappia et al. |
| 9,968,403 B2 | 5/2018 | Hasenberg et al. |
| 10,039,604 B2 | 8/2018 | Chia et al. |
| 10,067,304 B2 | 9/2018 | Yu et al. |
| 10,105,184 B2 | 10/2018 | Beck et al. |
| 10,175,435 B2 | 1/2019 | Peng et al. |
| 10,258,415 B2 | 4/2019 | Harrah et al. |
| 10,383,690 B2 | 8/2019 | Hodel et al. |
| 12,053,149 B2 | 8/2024 | Polejaev et al. |
| 2015/0224249 A1 | 8/2015 | Ciulla et al. |
| 2015/0230864 A1 | 8/2015 | Xuan et al. |
| 2015/0272674 A1 | 10/2015 | Xuan et al. |
| 2016/0081749 A1 | 3/2016 | Zhang et al. |
| 2016/0128553 A1 | 5/2016 | Geng |
| 2016/0166319 A1 | 6/2016 | Yu et al. |
| 2017/0363415 A1 | 12/2017 | Frisken |
| 2017/0366773 A1 | 12/2017 | Kiraly et al. |
| 2018/0092693 A1 | 4/2018 | Falkenstein et al. |
| 2018/0276877 A1* | 9/2018 | Mountney ........ A61B 1/000095 |
| 2019/0034976 A1 | 1/2019 | Hamedi et al. |
| 2019/0113700 A1 | 4/2019 | Peng et al. |
| 2019/0151022 A1 | 5/2019 | Yu et al. |
| 2019/0159839 A1 | 5/2019 | Zhang et al. |
| 2019/0192237 A1 | 6/2019 | Harrah et al. |
| 2019/0246908 A1 | 8/2019 | Pyun et al. |
| 2019/0298449 A1 | 10/2019 | Khachaturov et al. |
| 2019/0393669 A1 | 12/2019 | Yu et al. |
| 2020/0015668 A1 | 1/2020 | Scheib |
| 2020/0060537 A1* | 2/2020 | Rephaeli ............ G02B 23/2423 |
| 2020/0311917 A1 | 10/2020 | Segawa |
| 2021/0196384 A1 | 7/2021 | Shelton, IV et al. |
| 2021/0207942 A1 | 7/2021 | Winkelmann, Jr. et al. |
| 2022/0039632 A1 | 2/2022 | Polejaev et al. |
| 2023/0194248 A1 | 6/2023 | Watanabe et al. |
| 2023/0316639 A1* | 10/2023 | Buharin ................. G06T 15/06 345/426 |

FOREIGN PATENT DOCUMENTS

| | | |
|---|---|---|
| EP | 1582143 B1 | 9/2012 |
| EP | 3510962 A1 | 7/2019 |
| EP | 3512448 A1 | 7/2019 |
| EP | 3522811 A1 | 8/2019 |
| JP | 2004121546 A | 4/2004 |
| JP | 2016190002 A | 11/2016 |
| JP | 2016198304 A | 12/2016 |
| JP | 2018514237 A | 6/2018 |
| WO | WO-1990014797 A1 | 12/1990 |
| WO | WO-2016144382 A1 | 9/2016 |
| WO | WO-2019176121 A1 | 9/2019 |
| WO | WO-2020006454 A1 | 1/2020 |
| WO | WO-2020033121 A1 | 2/2020 |
| WO | WO-2022031793 A1 | 2/2022 |

OTHER PUBLICATIONS

"U.S. Appl. No. 17/393,710, Advisory Action mailed May 31, 2023", 3 pgs.
"U.S. Appl. No. 17/393,710, Examiner Interview Summary mailed Feb. 7, 2023", 2 pgs.
"U.S. Appl. No. 17/393,710, Final Office Action mailed Jan. 24, 2024", 29 pgs.
"U.S. Appl. No. 17/393,710, Final Office Action mailed Mar. 8, 2023", 40 pgs.
"U.S. Appl. No. 17/393,710, Non Final Office Action mailed Oct. 11, 2023", 42 pgs.
"U.S. Appl. No. 17/393,710, Non Final Office Action mailed Nov. 28, 2022", 38 pgs.
"U.S. Appl. No. 17/393,710, Notice of Allowance mailed Apr. 10, 2024", 9 pgs.
"U.S. Appl. No. 17/393,710, Response filed Feb. 8, 2023 to Non Final Office Action mailed Nov. 28, 2022", 11 pgs.
"U.S. Appl. No. 17/393,710, Response filed Feb. 28, 2024 to Final Office Action mailed Jan. 24, 2024", 8 pgs.
"U.S. Appl. No. 17/393,710, Response filed May 8, 2023 to Final Office Action mailed Mar. 8, 2023", 11 pgs.
"U.S. Appl. No. 17/393,710, Response filed Jun. 7, 2023 to Advisory Action mailed May 31, 2023", 11 pgs.
"U.S. Appl. No. 17/393,710, Response filed Dec. 7, 2023 to Non Final Office Action mailed Oct. 11, 2023", 11 pgs.
"Indian Application Serial No. 202347003197, First Examination Report mailed Jul. 25, 2023", 8 pgs.
"Indian Application Serial No. 202347003197, Response filed Nov. 30, 2023 to First Examination Report mailed Jul. 25, 2023", 28 pgs.
"International Application Serial No. PCT/US2021/044464, International Preliminary Report on Patentability mailed Feb. 16, 2023", 7 pgs.
"International Application Serial No. PCT/US2021/044464, International Search Report mailed Nov. 4, 2021", 4 pgs.
"International Application Serial No. PCT/US2021/044464, Written Opinion mailed Nov. 4, 2021", 5 pgs.
"Japanese Application Serial No. 2023-507794, Final Notification of Reasons for Refusal mailed Jul. 16, 2024", w/ English translation, 10 pgs.
"Japanese Application Serial No. 2023-507794, Notification of Reasons for Refusal mailed Feb. 5, 2024", w/ English Translation, 9 pgs.
"Japanese Application Serial No. 2023-507794, Response filed Apr. 26, 2024 to Notification of Reasons for Refusal mailed Feb. 5, 2024", W/English Claims, 16 pgs.
Shapiro Linda, et al., "Computer Vision", (Mar. 2000), 405-442.
"Japanese Application Serial No. 2023-507794, Response filed Oct. 11, 2024 to Final Notification of Reasons for Refusal mailed Jul. 16, 2024", W English Claims, 11 pgs.
"Indian Application Serial No. 202347003197, Hearing Notice mailed Jul. 8, 2025", 4 pgs.

* cited by examiner

DEPTH AND CONTOUR DETECTION FOR ANATOMICAL TARGETS

CROSS-REFERENCE TO RELATED APPLICATIONS

This application is a Continuation of U.S. patent application Ser. No. 17/393,710, filed Aug. 4, 2021, which claims the benefit of priority to U.S. Provisional Patent Application Ser. No. 63/061,249 filed Aug. 5, 2020, the contents of which are incorporated by reference in their entireties.

FIELD OF THE DISCLOSURE

The present disclosure relates to target identification and, more particularly to techniques for detecting contour and depth of an anatomical target

BACKGROUND OF THE DISCLOSURE

Medical scopes allow a user to inspect hidden areas of a patient. Certain medical scopes, such as endoscopes and laparoscopes, were first developed in the early 1800s and have been used to inspect inside the body of a patient. Medical scopes can include an optical sensor, such a camera for imaging an area at a distal end of the scope and controls located at an end proximal to the user for manipulating the distal end of the scope. A shaft can pass signals and can provide linkages between the proximal and distal ends of the scope. Some shafts can be flexible and some shafts can be rigid. Some medical scopes allow a user to pass tools or treatments down a channel of the shaft, for example, to resect tissue or retrieve objects.

Efficient use of a medical scope depends on several factors such as experience, dexterity, and visual cues. Medical scopes that allow for interaction within a small, confined space of a patient's body can use a screen or monitor to provide an image of the area located about the distal end of the medical scope.

SUMMARY OF THE DISCLOSURE

Improvement of the displayed image can help allow for better visual cues and thus, more efficient use of the medical scope. Techniques for detecting depth and contours of an anatomical target and for enhancing imaging of the anatomical target are described in this document. In an example, a pattern of light can be projected across an anatomical target and an image of the light pattern upon the anatomical target can be captured. The captured light pattern can be analyzed and used to help enhance a 2-dimensional image of the anatomical target.

This section is intended to provide an overview of subject matter of the present patent application. It is not intended to provide an exclusive or exhaustive explanation of the invention. The detailed description is included to provide further information about the present patent application.

DETAILED DESCRIPTION

During a medical procedure, such as an endoscopic procedure to apply therapy to tissue or to remove undesired material, such as a calculus ("stone") or a tumor, a physician can control the position of an optical fiber tip and resulting laser beam spot while viewing the real-time image captured by the endoscope camera. An approach can provide a camera image that is two dimensional (x, y) and but which does not provide scaled visualization in depth, or visual depth cues. Without visual depth cues, manipulate and positioning of the endoscope position, and optical fiber tip, in the axial depth direction can be difficult.

In endoscopic and laparoscopic procedures, success can depend on positioning of a distal end of the scope to achieve the desired results. In addition to aiming the end of the fiber tip at the anatomical target, the distance the fiber tip from the anatomical target can also affect the effectiveness of a round of therapy. A 2D imaging technology approach can provide good two-dimensional visual cues, but lacks providing effective 3rd-dimensional visual cues. In some cases, for example, of tumor removal, lack of good visual depth cues can prolong a medical treatment procedure, such as by requiring the physician to first employ a number of looks at the target tumor from various directions before then applying therapy. This approach involving number of looks from different directions is a tedious way for the user to assess the 3D nature of the tumor, the 3D nature of any healthy tissue near the tumor, or both.

Figure 1:
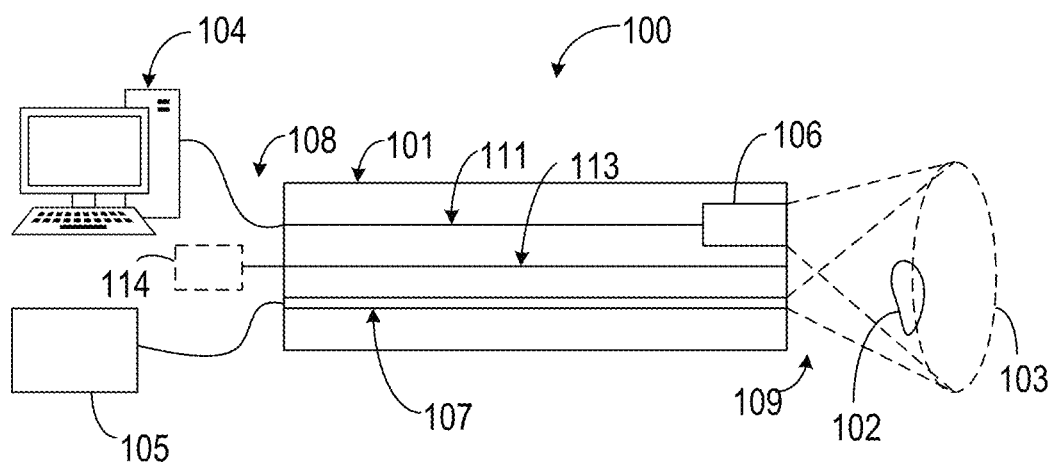
FIG. 1 illustrates generally an example system 100 for enhancing an image according to the present subject matter.

The present inventors describe, among other things, techniques to help improve 3-dimensional cues of a 2-dimensional image provided via a medical scope, especially visual depth cues and visual contour cues. FIG. 1 illustrates generally an example of portions of a system 100 for enhancing an image. The system 100 can include a medical scope 101 such as for viewing an anatomical target 102 or target area 103, an imaging system 104, and a pattern illumination system 105.

The medical scope 101 can provide a view of a target area 103 of the patient or a specific anatomical target 102. Examples of such medical scopes 101 can include but are not limited to, an endoscope, a laparoscope, or variations, and other types of scopes such as can be used for diagnostic or surgical procedures or both. The medical scope 101 can include a camera 106 or image sensor such as for electronically capturing representations of images of the target area 103 or anatomical target 102. The medical scope 101 can include one or more channels 107, 111, 113 such as for extending one or more instruments from one end, a proximal end 108, of the medical scope 101 to the other end, a distal end 109, of the medical scope 101. For example, a first channel 111 can include one or more wires or fibers such as for conducting or communicating information between the camera and the image system. The medical scope 101 can include or be coupled to an optional lighting source 114 such as for illuminating or flooding the target area 103 with light so the camera 106 can capture one or more images of the target area 103 and any anatomical targets 102. In such a configuration, a second channel 113 can provide an optical path for conveying the light from the proximal end 108 to the distal end 109 of the medical scope 101. A channel 107 of the medical scope 101 can provide an optical path such as for one or more optical fibers of a pattern illumination system 105. At the distal end of the channel 107, light from the one or more optical fibers can be projected toward the target area 103.

The pattern illumination system 105 can provide light for projecting a spatial light pattern across the target area 103 including across an anatomical target 102. The pattern illumination system 105 can include a laser or other light source. The projected light from the light source can be configured to form a specified projected pattern at the anatomical target 102 or target area 103. A specified first pattern of the light can have specified characteristics when projected on a flat surface of a given distance from the end of the channel 107 and reflected therefrom to provide a reference response pattern. Such characteristics can include, but are not limited to, spacing between attributes of the reference response pattern, thickness of shadows or pillars of light of the reference response pattern, etc. Upon being reflected from a non-flat surface, or a flat surface of a different distance from the end of the channel 107 than the given distance, etc. Upon being reflected from a non-flat surface, or a flat surface of a different distance from the end of the channel 107, the camera 106 can capture a second pattern of the reflected light via the one or more optical fibers.

The image system 104 can analyze the differences between the reflected response second pattern and the projected first pattern and, from such analysis, can detect and measure contour and depth information associated with the target area 103 or an anatomical target 102 in the target area 103. The image system 104 can then augment the 2-dimensional image, for example, with shading such as to add or accentuate 3-dimensional cues that can be included with the 2-dimensional image to visually distinguish depth and contour information. The shading can include visual modulation of light intensity or spatial modulation of light to indicate depth or a contour, for example.

The added or accentuated 3-dimensional cues can help provide useful spatial context to the user, which, in turn, can help enable the user to obtain better 3-dimensional positioning of the distal end of the medical scope 101, or of one or more instruments utilized with the medical scope 101. This can help avoid or to reduce or minimize the number of different directional "looks" that may otherwise be needed by the user in order to perform a successful procedure, such as a laser therapy procedure.

Figure 2A:
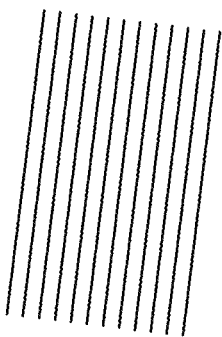
FIGS. 2A-2D illustrate generally effects of projecting a spatial light pattern on an anatomical target.
Figure 2B:
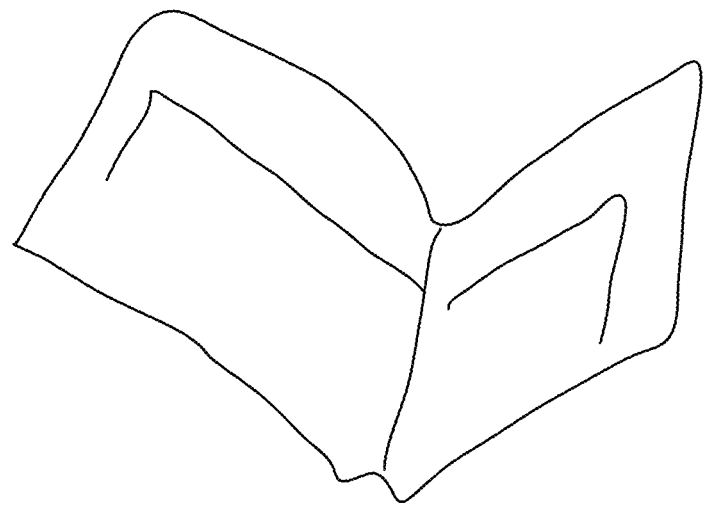
Figure 2D:
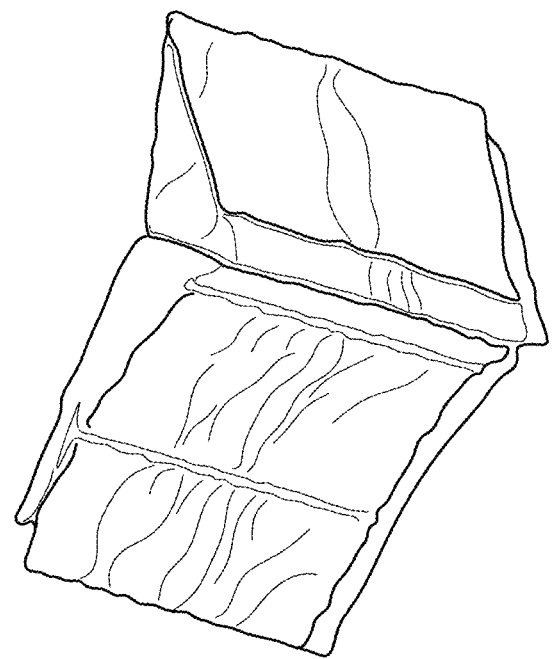
Figure 2C:
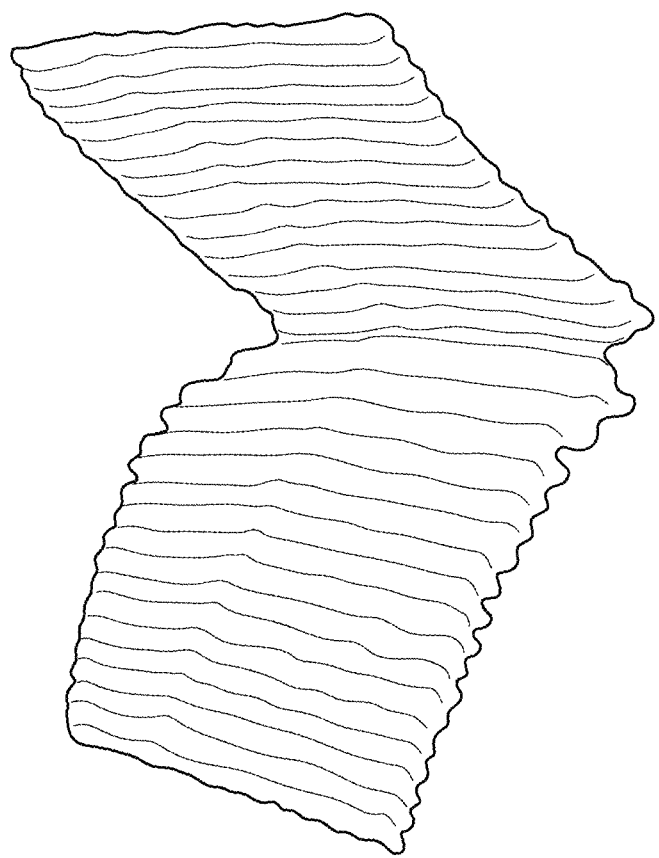

FIGS. 2A-2D illustrate generally effects of projecting a light pattern on an anatomical target. FIG. 2A illustrates an example of a light pattern that can be cast upon a flat surface from an illumination system employed with the medical scope. The pattern can include a specified pattern of lines, such as of a certain spacing and thickness, when projected onto an orthogonal flat surface. In some examples, spacing and thickness can be substantially equal when projected onto an orthogonal flat surface, such as to provide one or more of equal spacings between lines, equal thickness of lines, or both spacings and thicknesses being equal to each other. However, if a pattern is cast upon a surface or surface portion that is not orthogonal but is instead at a non-zero angle to the orthogonal flat surface, the thickness and spacing of the lines can vary depending on the magnitude, direction, or orientation of the angle and the direction of the projected lines with respect to such angle. FIG. 2B illustrates generally a 2-dimensional image of an anatomical target (e.g., kidney stone or a tumor) as it may appear on a screen of an imaging system employed with a medical scope. The 2-dimensional image can show the user a very good outline of the stone or tumor but may not provide any additional 3D cues. FIG. 2C illustrates generally the tumor or kidney stone of FIG. 2B with a light pattern, such as the light pattern of FIG. 2A, cast across the tumor or kidney stone. The light pattern reflected from the surface of the stone, as well as, the background of the area, can help bring out 3D artifacts of the anatomical target and target area that may be hidden in the 2-dimensional image because of glare, texture fluctuations, lighting angle, etc. The 3D cues are visible due to the distortion of the lines of the reflected light pattern compared to, for example, the reference response pattern or the projected pattern such as the pattern of FIG. 2A. In certain examples, an image system can analyze one or more of the line fluctuations and changes in line thickness and line spacing to provide 3D information about the target. The imaging system can enhance the 2-dimensional image based on the 3D information to provide an enhanced 2-dimensional image with 3D cues for the viewer as is illustrated in FIG. 2D. For example, the enhanced view provided by the imaging system can include additional or enhanced shading to bring out the 3D cues. In some examples, the enhanced view does not include the line pattern. In some examples, the enhanced view can include visual and text-based indications of data associated with the orientation of a fiber of an instrument with respect to the anatomical target. Such data can include but is not limited to, distance between the tip of the fiber and the surface of the anatomical target, angle of the surface with respect to the trajectory of the fiber, etc. In certain examples, information enabling conversion of the 2D image to a 3D image can be displayed.

Figure 3:
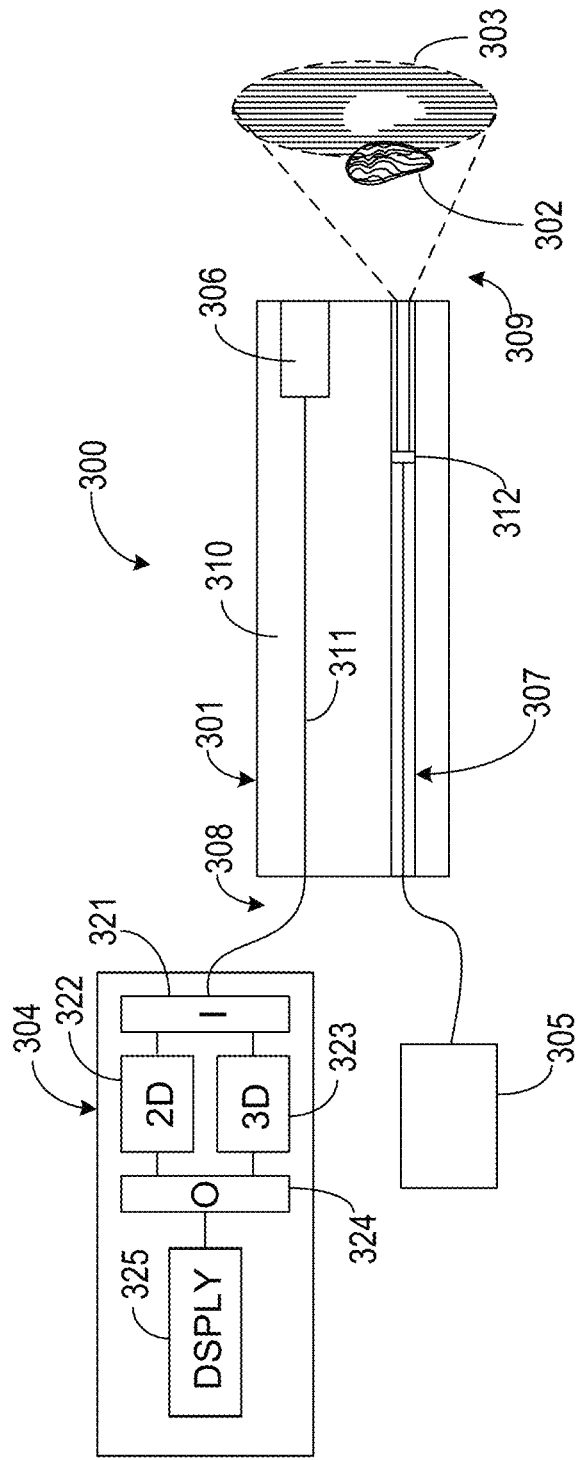
FIG. 3 illustrates generally details of an example system 300 for enhancing an image according to the present subject matter.

FIG. 3 illustrates generally details of a portion of an example system 300 for enhancing an image according to the present subject matter. In certain examples, the system 300 of FIG. 3 can be a more detailed view of the example system 100 of FIG. 1. The system 300 can include a medical scope 301 for viewing an anatomical target 302 or target area 303, an imaging system 304, and a pattern illumination system 305. In certain examples, the system 300 or the medical scope can include a second illumination source (not shown) for illuminating or flooding the target area 303 with light so the imaging system can capture images of the target area 303 and any anatomical targets 302. The medical scope 301 can include a shaft 310 for extension into an orifice of the patient or through an incision of the patient. The shaft 310 can include multiple channels 307, 311 and an optical sensor 306. A first channel 311 can be used to convey image signals from the optical sensor 306 located at the distal end 309 of the shaft 310 to the image system 304 coupled to the proximal end 308 of the shaft 310. A second channel 307 can be used as an optical path to convey light of the pattern illumination system 305 to the anatomical target 302 or target area 303 for the purpose of projecting a pattern of the light across the anatomical target 302 or target area 303. At the distal end 309 of the shaft 310, the light can be projected from the optical path via two locations or two areas. The purpose of projecting the light toward the anatomical target 302 from two points is to allow the light from each point to interfere with each other to form an interference pattern across the field of view or target area 303. In certain examples, polarized light projected across the anatomical target from two distinct areas of the optical path can form a clear interference pattern. Enhanced clarity can be provided using the polarization of the light. Further clarity of the pattern can be achieved using coherent and polarized light compared to using non-coherent and unpolarized light.

In certain examples, the second channel 307 can include a beam splitter 312 to form two beams of light from a single beam of light of the light source of the pattern illumination system 305. For example, light of the light source can be conveyed via a single optical media, such as an optical cable or optical fiber, from the light source of the pattern illumination system 305 to the beam splitter 312. At the beam splitter 312, the light can be further conveyed to the distal end 309 as two different beams via two optical paths. In some examples, the distal end 309 of the optical path can project each of the two beams of light such that the light appears to be projecting through two slits at the end of the optical path to provide the interference pattern. In certain examples, the light can be conveyed from the pattern illumination system 305 via single mode optical fiber or single mode optical fiber cable.

The imaging system 304 can capture image information from a signal provided from the optical sensor 306. In certain examples, the imaging system 304 can include an input processing circuit 321, a 2D image processing circuit 322, a 3D artifact circuit 323, and a display interface circuit 324. The input processing circuit 321 can separate the image information into first image information associated with providing a 2D image of the anatomical target 302 or target area 303 and second image information associated with the interference pattern as captured on the surface of the anatomical target 302 or target area 303. The 2D image processing circuit 322 can process the first image information for reception at the display interface circuit 324. The 3D artifact circuit 323 can process the second image information for enhancing the 2D image. For example, the 3D artifact circuit 323 can analyze the interference pattern of the second image information, including comparing and measuring deviations of the interference pattern with a reference pattern to extract 3D cues about the anatomical target 302 or target area 303. The analysis can allow the display interface circuit 324 to enhance the 2D image information received from the 2D image processing circuit 322 with information provided by the 3D artifact circuit 323 to guide image enhancement techniques to provide or bring out the 3D cues in an enhanced 2D image. In certain examples, the techniques can include altering or adding shadowing or coloring of the 2D image based on the interference pattern to provide an enhanced 2D image. The enhanced 2D image can be displayed on a monitor 325 of the imaging system to assist the user of the medical scope 301 in positioning the distal end of the medical scope 301 with respect to an anatomical target, as well as, positioning therapy instruments with respect to an anatomical target for effective and efficient use of the therapy.

Figure 4:
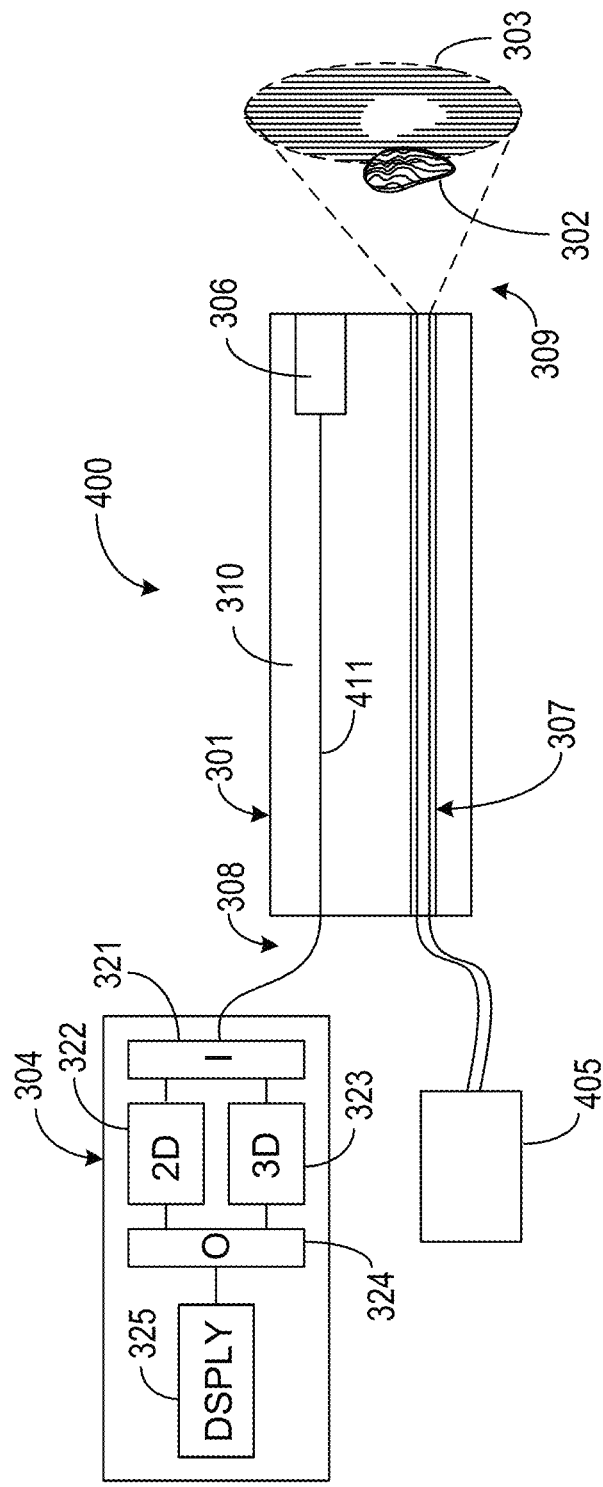
FIG. 4 illustrates generally an example system 400 for enhancing 3D cues of an image provided using a medical scope 301.

FIG. 4 illustrates generally an example system 400 for enhancing 3D cues of an image provided using a medical scope 301. The system 400 of FIG. 4 is a modification of the system 300 of FIG. 3. In certain examples, the system 400 of FIG. 4 can be a more detailed view of the example system 100 of FIG. 1. The system 400 can include a medical scope 301 for viewing an anatomical target 302 or target area 303, an imaging system 304, and a pattern illumination system 405. The medical scope 301 can include a shaft 310 for extension into an orifice of the patient or through an incision of the patient. The shaft 310 can include multiple channels 307, 311 and an optical sensor 306. A first channel 311 can be used to convey image signals from the optical sensor 306 located at the distal end 309 of the shaft 310 to the image system 304 coupled to the proximal end 308 of the shaft 310. A second channel 307 can be used as an optical path to convey light of the pattern illumination system 305 to the anatomical target 302 or target area 303 for the purpose of projecting a pattern of the light across the anatomical target 302 or target area 303. At the distal end 309 of the shaft 310, the light can be projected from the optical path via two points or two areas. The purpose of projecting the light toward the anatomical target 302 from two points is to allow the light from each point to interfere with each other to form an interference pattern across the field of view or target area 303. In certain examples, polarized light projected across the anatomical target from two distinct areas of the optical path can form a clear interference pattern. The clarity comes from the polarization of the light. Further clarity of the pattern can be achieved using coherent and polarized light compared to using non-coherent and unpolarized light.

In certain examples, instead of a beam splitter, the light from the pattern illumination system can be conveyed through the second channel 307 via two isolated optical media, such as two optical fibers, to form two beams of light from the light source of the pattern illumination system 405. In some examples, the distal end 309 of the optical path can project each of the two beams of light such that the light appears to be projecting through two slits at the end of the optical path. In certain examples, the light can be conveyed from the pattern illumination system 405 via a single mode optical fibers or single mode optical fiber cables.

The imaging system 304 can capture image information from a signal provided from the optical sensor 306. In certain examples, the imaging system 304 can include an input processing circuit 321, a 2D image processing circuit 322, a 3D artifact circuit 323, and a display interface circuit 324. The input processing circuit 321 can separate the image information into first image information associated with providing a 2D image of the anatomical target 302 or target area 303 and second image information associated with the interference pattern as captured on the surface of the anatomical target 302 or target area 303. The 2D image processing circuit 322 can process the first image information for reception at the display interface circuit 324. The 3D artifact circuit 323 can process the second image information for enhancing the 2D image. For example, the 3D artifact circuit 323 can analyze the interference pattern of the second image information, including comparing and measuring deviations of the interference pattern with a reference pattern to extract 3D cues about the anatomical target 302 or target area 303. The analysis can allow the display interface circuit 324 to enhance the 2D image information received from the 2D image processing circuit 322 with information provided by the 3D artifact circuit 323 to guide techniques to bring out the 3D cues in a new 2D image. In certain examples, the techniques can include altering or adding shadowing of the 2D image based on the interference pattern to provide an enhanced 2D image. The enhanced 2D image can be displayed on a monitor 325 of the imaging system to assist the user of the medical scope 301 in positioning the distal end of the medical scope 301 with respect to an anatomical target, as well as, positioning therapy instruments with respect to an anatomical target for effective and efficient use of the therapy.

FIGS. 3 and 4 illustrate using interference to generate the light pattern projected onto the anatomical target. Other methods of generating the pattern are also possible including using a pattern filter to project the light pattern such that the pattern filter can block light to cast a pattern of light and shadow onto the anatomical target. Such a filter can include a layer of glass that includes the pattern filter. In some examples, the system can include a scanning laser that can direct, scan, or continuously move a laser beam in a pattern to project the pattern onto the anatomical target.

Figure 5:
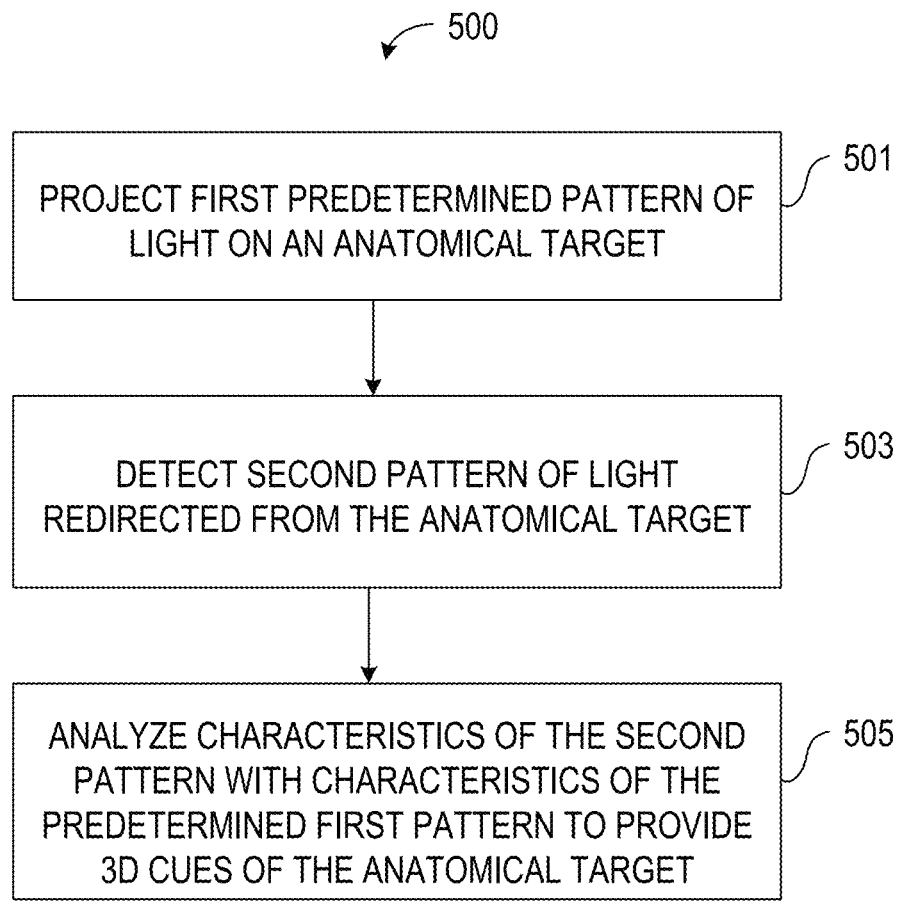
FIG. 5 illustrates generally an example method of enhancing a 2D image of an anatomical target to provide 3D cues.

FIG. 5 illustrates generally an example method of enhancing a 2D image of an anatomical target to provide 3D cues. At 501, a first, specified pattern of light can be cast on an anatomical target. The first pattern of light, when cast upon a specified surface at a specified distance will have specified characteristics including, among other things, specified dimensions regarding distances between lines of the pattern, and specified thicknesses of light areas and shadow or dark areas of the pattern. At 503, as second pattern can be detected and captured by an optical sensor. The second pattern can be a result of reflection of the first pattern off the surface of the anatomical target. At 505, characteristics of the second pattern can be analyzed with reference to characteristics of the first pattern. Analysis may include creating data points of characteristic deviations of the second pattern from the first pattern and deriving depth and contour information of the anatomical target from the data points such that 3D cues about the surface of the anatomical target can be detected and captured. Such 3D cues can be derived by an imaging system and can be used to provide an enhanced 2D image of the anatomical target for display to the user of an endoscope or laparoscope, for example.

In certain examples, an enhanced 2D image that includes additional 3D cues about an anatomical target accessible via a medical scope can further assist a user with visualization of the anatomical target and surrounding area as a laparoscopic or endoscopic procedure progresses. In certain examples, the illumination pattern used to detect depth and contours of an anatomical target during a procedure are not visible on the enhanced 2D image so as not to interfere with the visualization. The enhanced visualization can assist in shortening procedures as the 3D cues can help a user reduce the number of "look" movements of a procedure. In certain examples, the additional 3D cues can assist in reducing mental fatigue compared to a user using a non-enhanced 2D image of an anatomical target. In some examples, the 3D cues of the enhanced 2D image can assist in providing more effective therapy. For example, when treating tumors via laser therapy, depth of the therapy can be controlled by applying the laser therapy at a certain distance from the anatomical target surface of the tumor and at an angle to the tumor surface. An angle less perpendicular to the plane of the tumor surface typically results in less depth of applied therapy. The enhanced 2D image provided in accordance with the present subject matter can provide cues about the contours and undulations of the tumor surface such that the angle of the therapy can be adjusted to account for the contours and undulations which can result in more precise application of the therapy.

Notes and Examples

In a first example, Example 1, an image enhancement system to enhance a 2-dimensional display image, the image enhancement system can include a first illumination source; a first optical path configured to project a first pattern of light provided by the first illumination source at a surface of an anatomical target; a sensor configured to detect light reflected from the surface and transmit an image signal, the image signal based on the light reflected from the surface; and an imaging system configured to receive the image signal, to detect a second pattern of light reflected from the surface and to determine contour information of the surface of the anatomical target based on the second pattern of light.

In Example 2, the subject matter of Example 1 includes, wherein the first illumination source is configured to generate coherent light.

In Example 3, the subject matter of Examples 1-2 includes, wherein the first illumination source is configured to generate polarized light.

In Example 4, the subject matter of Example 3 includes, wherein the first optical path is configured to project at least two distinct beams of light toward the surface; and wherein the first pattern is an interference pattern of the at least two distinct beams at the surface.

In Example 5, the subject matter of Example 4 includes, wherein the first illumination light source is configured to project a single beam of light; and wherein the first optical path includes a beam splitter to provide the at least two distinct beams.

In Example 6, the subject matter of Examples 1-5 includes, wherein the first optical path is configured to extend through an endoscope or laparoscope to the anatomical target.

In Example 7, the subject matter of Examples 1-6 includes, wherein the imaging system includes a display; and wherein the imaging system is configured to visually distinguish the contour information via the display.

In Example 8, the subject matter of Example 7 includes, D representation includes the image with adjusted shading based on the contour information.

In Example 9, the subject matter of Examples 1-8 includes, a second illumination light source configured to illuminate the anatomical target with second light via a second optical path.

Example 10 is a method of detecting 3-dimensional (3D) cues from an anatomical target, the method comprising: projecting a first pattern of light on the anatomical target, the first pattern of light configured to display specified characteristics in response to application upon a reference target; detecting, at an optical sensor, a second pattern of light redirected from the anatomical target; and analyzing characteristics of the second pattern with the specified characteristics to provide contour information of the anatomical target.

In Example 11, the subject matter of Example 10 includes, D cues based on the contour information.

In Example 12, the subject matter of Example 11 includes, D image does not include the second pattern.

In Example 13, the subject matter of Examples 10-12 includes, wherein projecting the first pattern includes illuminating the anatomical target with two distinct beams of polarized light.

In Example 14, the subject matter of Example 13 includes, wherein the first pattern is formed from interference of a first beam of the two beams of polarized light with a second beam of the two beams of polarized light.

In Example 15, the subject matter of Example 14 includes, wherein the polarized light is coherent light.

In Example 16, the subject matter of Examples 10-15 includes, wherein the projecting the first pattern includes generating a laser beam to form the first pattern. In Example 17, the subject matter of Example 16 includes, wherein the projecting the first pattern includes splitting the laser beam into two beams of laser light using a beam splitter located within a channel of an endoscope or laparoscope.

In Example 18, the subject matter of Example 17 includes, wherein the projecting includes projecting the two beams at the anatomical target from ends of two optical media at a distal end of the endoscope or laparoscope.

In Example 19, the subject matter of Examples 10-18 includes, wherein the detecting the second pattern includes detecting the second pattern at an optical sensor positioned at a distal end of an endoscope or laparoscope.

In Example 20, the subject matter of Example 19 includes, wherein the projecting a first pattern of light on the anatomical target include projecting a first pattern of light from a first illumination source on the anatomical target; and wherein the method includes illuminating the target using a second illumination source, wherein the second illumination source is part of an endoscopic or laparoscopic system.

Example 21 is at least one machine-readable medium including instructions that, when executed by processing circuitry, cause the processing circuitry to perform operations to implement of any of Examples 1-20.

Example 22 is an apparatus comprising means to implement of any of Examples 1-20.

Example 23 is a system to implement of any of Examples 1-20.

Example 24 is a method to implement of any of Examples 1-20.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, the terms "including" and "comprising" are open-ended, that is, a system, device, article, composition, formulation, or process that includes elements in addition to those listed after such a term are still deemed to fall within the scope of subject matter discussed. Moreover, such as may appear in a claim, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72 (b), to allow the reader to quickly ascertain the nature of the technical disclosure. It is submitted with the understanding that it will not be used to interpret or limit the scope or meaning of a claim. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. The following aspects are hereby incorporated into the Detailed Description as examples or embodiments, with each aspect standing on its own as a separate embodiment, and it is contemplated that such embodiments can be combined with each other in various combinations or permutations.

What is claimed is:

1. An image enhancement system for enhancing a two-dimensional display image, the image enhancement system comprising:
    image processing circuitry configured to perform operations, the operations comprising:
        receiving an image signal that represents a two-dimensional camera image of a surface of an anatomical target being illuminated by light having a first pattern of lines;
        detecting, from the two-dimensional camera image, a second pattern of lines, the second pattern of lines including at least some lines that are distorted in at least one of spacing or thickness compared to the first pattern of lines;
        determining contour information of the surface of the anatomical target based on the distortion of the second pattern of lines compared to the first pattern of lines; and
        generating an enhanced two-dimensional image that includes the two-dimensional camera image with adjusted shading based on the contour information.

2. The image enhancement system of claim 1, wherein the image processing circuitry is configured to perform operations for generating the enhanced two-dimensional image to include three-dimensional cues based on the contour information and to not include the second pattern of lines.

3. The image enhancement system of claim 1, further comprising:
    a first illumination source configured to project the light having the first pattern of lines at the surface of the anatomical target via a first optical path that extends through an endoscope or a laparoscope to the anatomical target.

4. The image enhancement system of claim 3, wherein the first illumination source is configured to generate coherent, polarized light.

5. The image enhancement system of claim 3, further comprising:
    a second illumination source configured to illuminate the anatomical target via a second optical path.

6. The image enhancement system of claim 5, wherein the second illumination source is part of an endoscopic or laparoscopic system that includes the endoscope or the laparoscope.

7. The image enhancement system of claim 3, further comprising:
    a camera configured to generate the image signal from the two-dimensional camera image of the surface of the anatomical target being illuminated by the first pattern of lines.

8. The image enhancement system of claim 7, wherein the camera is positioned at a distal end of the endoscope or the laparoscope.

9. The image enhancement system of claim 7, wherein the camera is located directly adjacent to the anatomical target with no intervening optical elements between the camera and the anatomical target.

10. The image enhancement system of claim 1, further comprising:
a display configured to display the enhanced two-dimensional image.

11. A method for enhancing a two-dimensional display image, the method comprising:
receiving, with processing circuitry, an image signal that represents a two-dimensional camera image of a surface of an anatomical target being illuminated by light having a first pattern of lines;
detecting, with the processing circuitry, from the two-dimensional camera image, a second pattern of lines, the second pattern of lines including at least some lines that are distorted in at least one of spacing or thickness compared to the first pattern of lines;
determining, with the processing circuitry, contour information of the surface of the anatomical target based on the distortion of the second pattern of lines compared to the first pattern of lines; and
generating, with the processing circuitry, an enhanced two-dimensional image that includes the two-dimensional camera image with adjusted shading based on the contour information.

12. The method of claim 11, wherein the enhanced two-dimensional image includes three-dimensional cues based on the contour information and does not include the second pattern of lines.

13. The method of claim 11, further comprising:
projecting, with a first illumination source, the light having the first pattern of lines at the surface of the anatomical target via a first optical path that extends through an endoscope or a laparoscope to the anatomical target.

14. The method of claim 13, further comprising:
illuminating the anatomical target, via a second optical path, with a second illumination source that is part of an endoscopic or laparoscopic system that includes the endoscope or the laparoscope.

15. The method of claim 13, further comprising:
generating, with a camera, the image signal from the two-dimensional camera image of the surface of the anatomical target being illuminated by the light having the first pattern of lines, the camera being positioned at a distal end of the endoscope or the laparoscope, the camera being located directly adjacent to the anatomical target with no intervening optical elements between the camera and the anatomical target.

16. A non-transitory computer-readable storage medium storing instructions for enhancing a two-dimensional display image, the instructions, when executed by processing circuitry, cause the processing circuitry to perform operations, the operations comprising:
receiving, with processing circuitry, an image signal that represents a two-dimensional camera image of a surface of an anatomical target being illuminated by light having a first pattern of lines;
detecting, with the processing circuitry, from the two-dimensional camera image, a second pattern of lines, the second pattern of lines including at least some lines that are distorted in at least one of spacing or thickness compared to the first pattern of lines;
determining, with the processing circuitry, contour information of the surface of the anatomical target based on the distortion of the second pattern of lines compared to the first pattern of lines; and
generating, with the processing circuitry, an enhanced two-dimensional image that includes the two-dimensional camera image with adjusted shading based on the contour information.

17. The non-transitory computer-readable storage medium of claim 16, wherein the enhanced two-dimensional image includes three-dimensional cues based on the contour information and does not include the second pattern of lines.

18. The non-transitory computer-readable storage medium of claim 16, wherein the operations further comprise:
projecting, with a first illumination source, the light having the first pattern of lines at the surface of the anatomical target via a first optical path that extends through an endoscope or a laparoscope to the anatomical target.

19. The non-transitory computer-readable storage medium of claim 18, wherein the operations further comprise:
illuminating the anatomical target, via a second optical path, with a second illumination source that is part of an endoscopic or laparoscopic system that includes the endoscope or the laparoscope.

20. The non-transitory computer-readable storage medium of claim 18, wherein the operations further comprise:
generating, with a camera, the image signal from the two-dimensional camera image of the surface of the anatomical target being illuminated by the light having the first pattern of lines, the camera being positioned at a distal end of the endoscope or the laparoscope, the camera being located directly adjacent to the anatomical target with no intervening optical elements between the camera and the anatomical target.

* * * * *